United States Patent [19]
Douglas et al.

[11] Patent Number: 6,144,922
[45] Date of Patent: Nov. 7, 2000

[54] ANALYTE CONCENTRATION INFORMATION COLLECTION AND COMMUNICATION SYSTEM

[75] Inventors: Joel S. Douglas, Santa Clara; Andrew M. Drexler, Los Altos Hills; Charles C. Raney, Scotts Valley; Edward C. Leung, Cupertino; Edison F. Yee, Los Altos, all of Calif.

[73] Assignee: Mercury Diagnostics, Incorporated, Scotts Valley, Calif.

[21] Appl. No.: 08/963,674

[22] Filed: Oct. 31, 1997

[51] Int. Cl.⁷ ........................................... A61B 5/08
[52] U.S. Cl. ............................... 702/31; 128/904
[58] Field of Search .............................. 600/347; 128/920, 128/904; 702/22, 19; 340/870.01, 870.06, 875.06

[56] References Cited

U.S. PATENT DOCUMENTS

| | | | |
|---|---|---|---|
| 4,546,436 | 10/1985 | Schneider et al. | 364/415 |
| 5,025,374 | 6/1991 | Roizen et al. | 364/413.02 |
| 5,549,117 | 8/1996 | Tacklind et al. | 128/716 |
| 5,771,891 | 6/1998 | Gozani | 128/635 |
| 5,840,020 | 11/1998 | Heinomen et al. | 600/309 |
| 5,878,384 | 3/1999 | Johnson et al. | 702/187 |
| 5,899,855 | 5/1999 | Brown | 600/302 |

*Primary Examiner*—Timothy P. Callahan
*Assistant Examiner*—Linh Nguyen
*Attorney, Agent, or Firm*—Burns Doane Swecker & Mathis LLP

[57] ABSTRACT

A monitoring system which collects patient physiological date is designed specifically for communication with a communication module which facilitates data transfer from the monitoring system to a remote site. The communication module has data input mechanisms to facilitate setting parameters of the monitoring system and/or the communication module. The communication module is provided with a modem member which is used to communicate with the remote site and an optional data exchange module which is designed to communicate the same information with a local computer system. The remote site may be a bulletin board system or internet site where the monitoring information can be stored by the patient using the monitoring system by patient identification or name and include monitoring readings, time and date stamp, conditions such as meal times, exercise times and therapy amounts and their associated date and time.

59 Claims, 6 Drawing Sheets

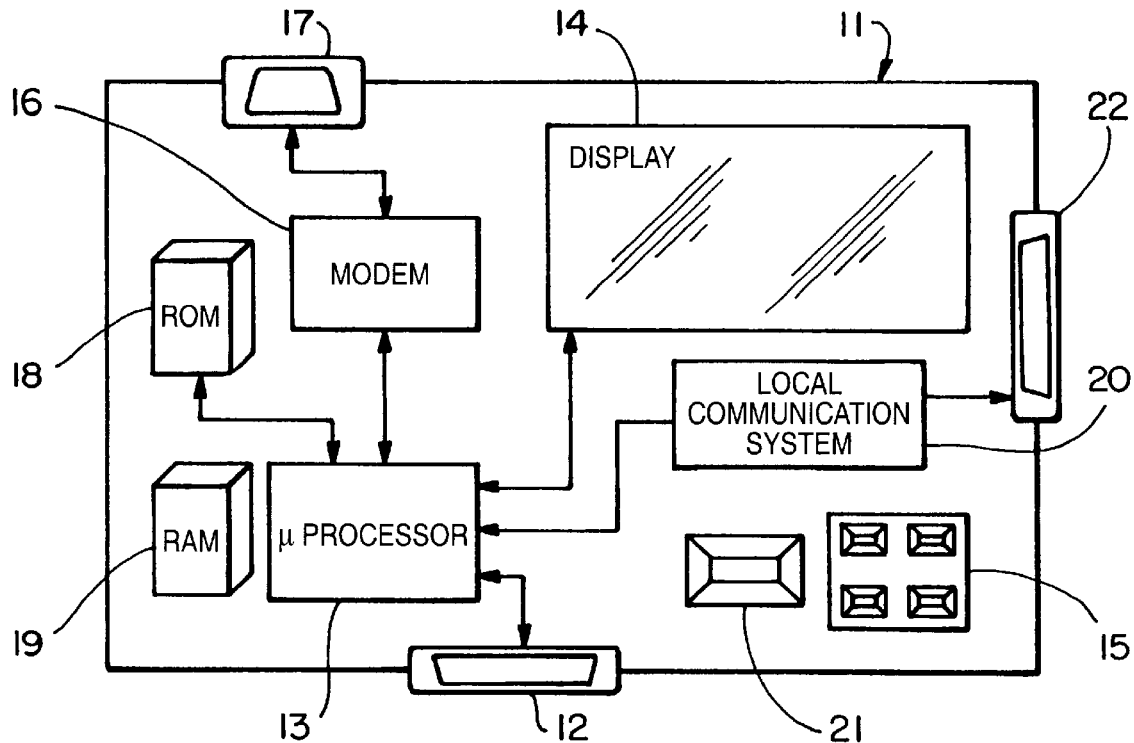
FIG._1
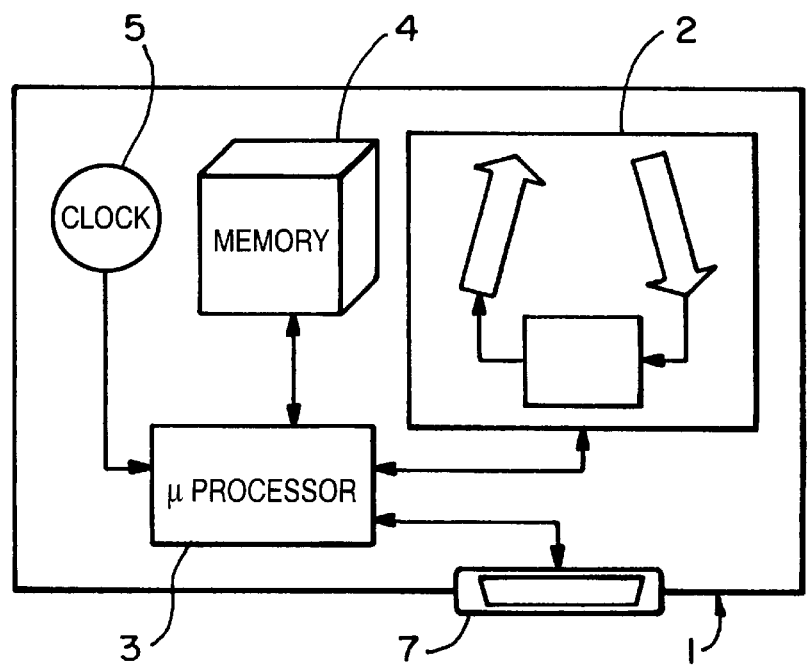
FIG._2

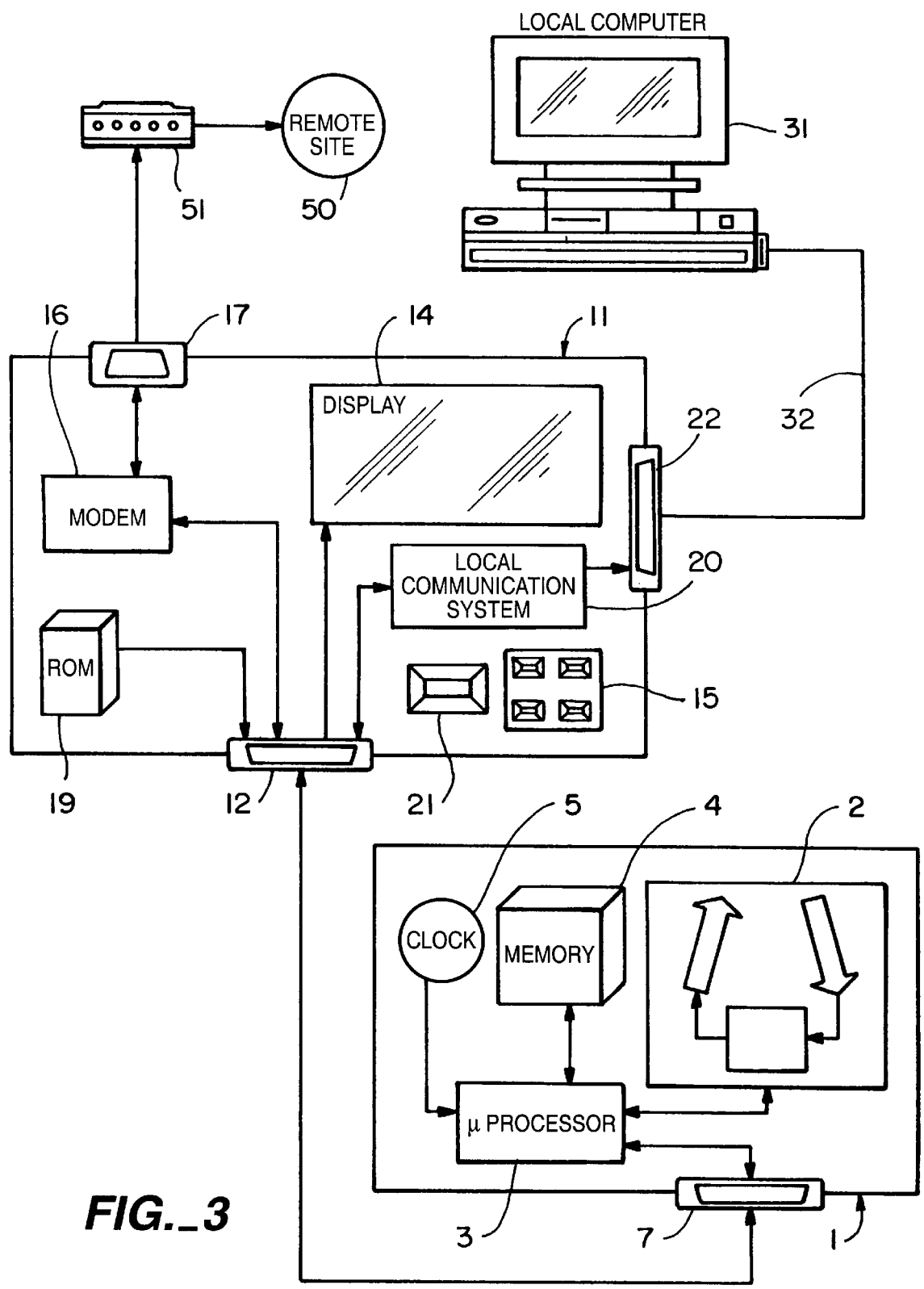
FIG._3

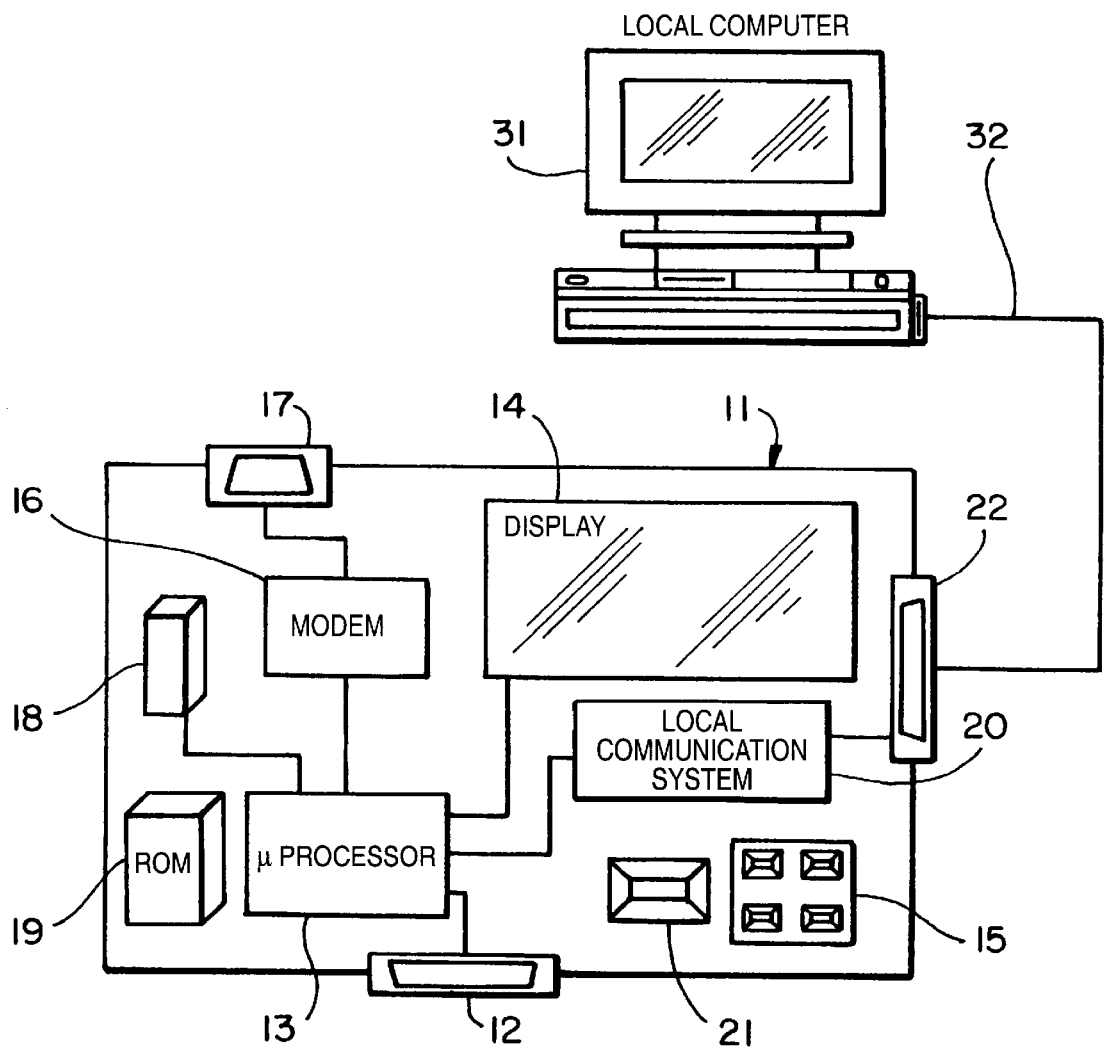
FIG._4

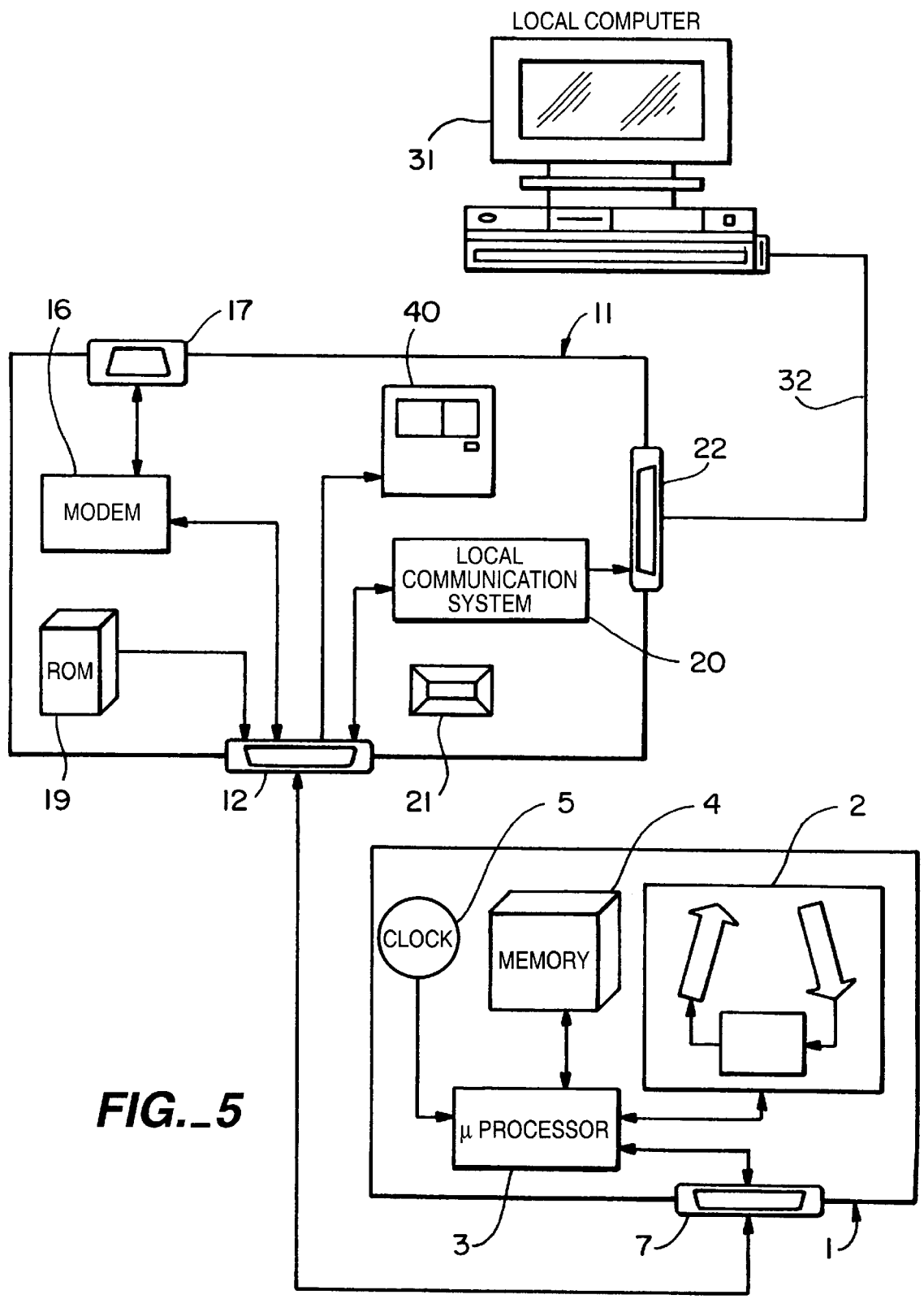
FIG._5

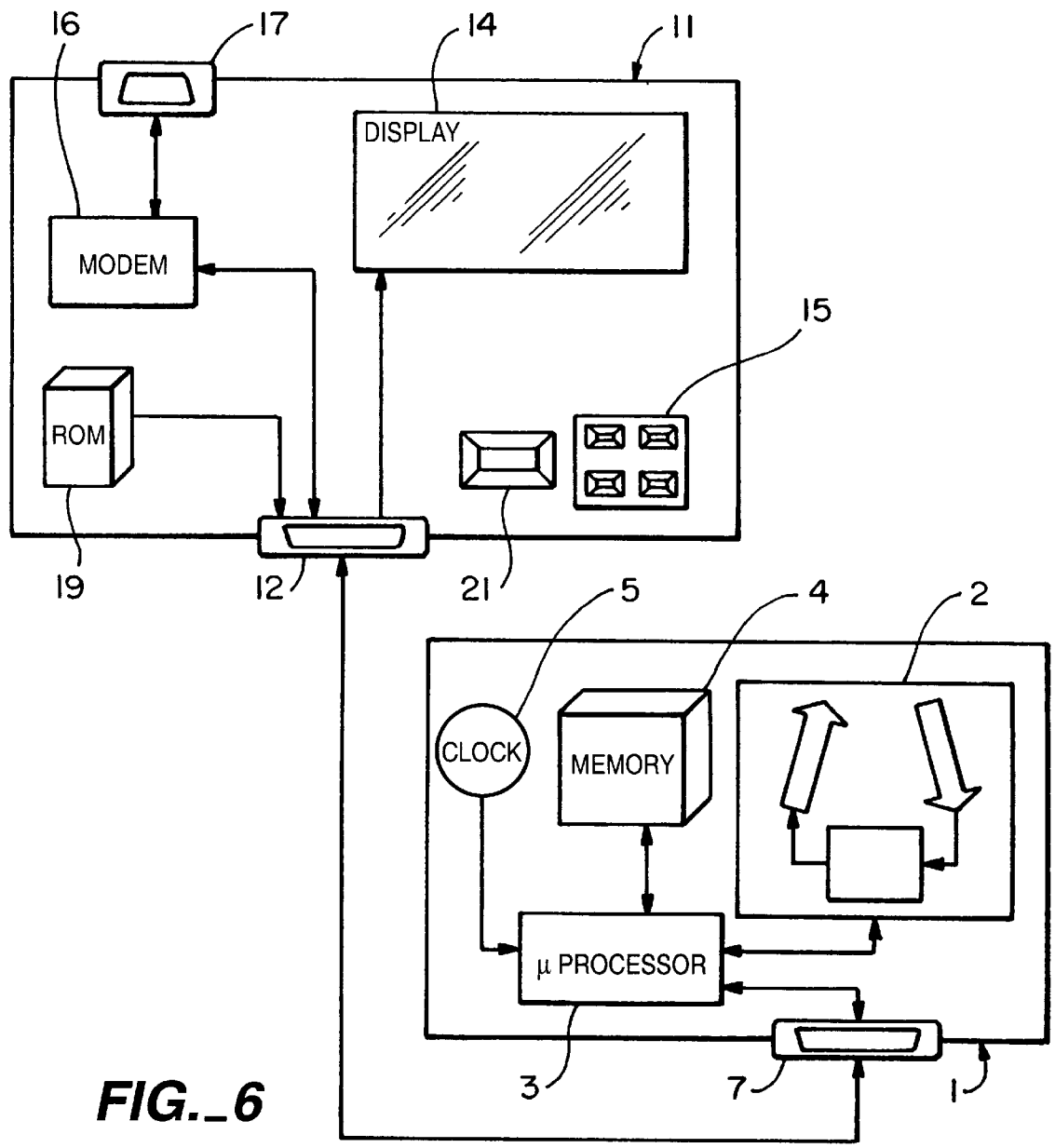
FIG._6

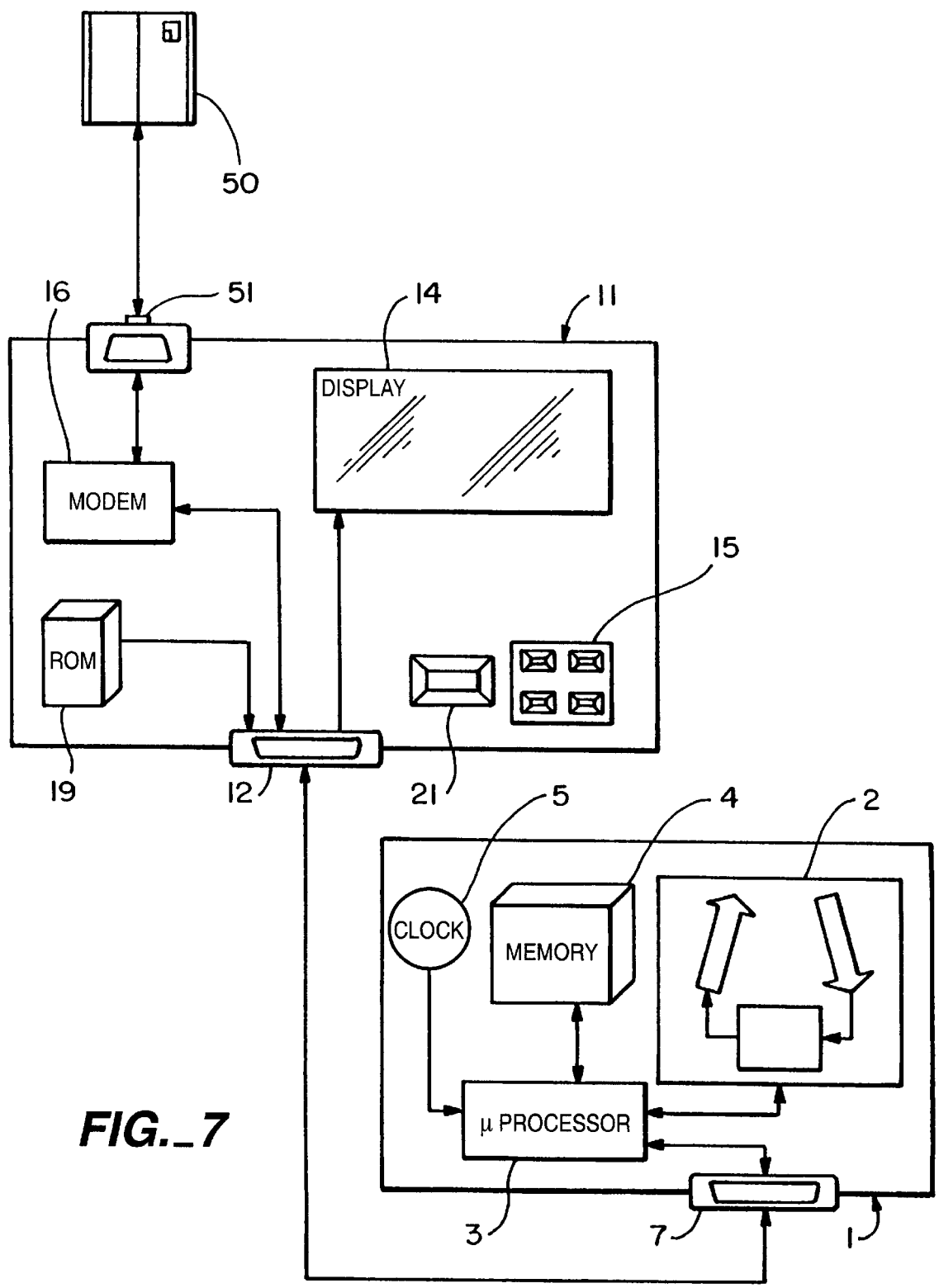
FIG._7

ANALYTE CONCENTRATION INFORMATION COLLECTION AND COMMUNICATION SYSTEM

BACKGROUND OF THE INVENTION

1. Field of the Invention

The invention relates to the collection and communication of analyte concentration information, and more particularly, to a system for gathering and communicating such data for analysis and treatment.

2. Description of Related Art

Numerous simple test devices have been developed to test for presence and quantity of analytes in aqueous samples, particularly whole blood. The patent and technical literature of the last thirty years is replete with inventions which utilize a dry chemistry reagent system or electrochemical methods to test for analytes in bodily fluids. These systems have been designed so that they can capture various pieces of data such as time of day, date, calorie intake, exercise time and associated glucose readings.

A large government-sponsored study (the DCCT) demonstrated conclusively that careful control of blood glucose levels can significantly reduce the incidence of serious complications of diabetes such as vision loss and kidney malfunction. Most diabetics must test themselves periodically in order to make appropriate adjustments to their diet or medication. Thus, it is especially important for diabetics to have a simple and accurate means to capture their blood glucose readings and provide them to their health care provider for analysis of long-term control.

The technologies embodied in the products which have been developed to date all have certain limitations from the perspective of the end user and/or the manufacturer. The following review of prior art illustrates some of the many adaptations of the approaches which may be found in the patent literature. Numerous types of data collection systems have been utilized to capture reading from test devices for long-term analysis and therapy modulation. Many of these devices have been developed to interface with a local computer system and or upload the information to a disease management system.

Disease management system and the methods for data capture are taught in numerous patents and other prior art. U.S. Pat. No. 5,307,263 to Brown teaches a method which uses various monitors and a data management unit, a hand held unit and a modem to communicate with a clearing house and or user's computer.

U.S. Pat. No. 5,025,374 to Roizen et al. teaches a method of making and using an interactive medical test selector for use by a patient. It includes a memory device for storing the patient responses.

U.S. Pat. No. 4,731,726 to Allen III et al. teaches a method of monitoring a patient using a measuring device linked to a monitoring apparatus capable of receiving and storing data and using this information to generate insulin dosage recommendations.

U.S. Pat. No. 4,546,436 to Schneider et al. teaches the use of a device for continuous recording of physiological data. The system includes a data mapping and compression technique which permits long-term data acquisition.

U.S. Pat. No. 4,531,527 to Reinholdr et al. teaches a cardiac monitoring system which interfaces with an EKG and an office unit which can process the collected data.

U.S. Pat. No. 4,803,625 to Fu et al. describes a personal health monitor which includes sensors and is coupled to a central unit via modems and a computer which is programmed to prompt a patient to take prescribed medication at specific times.

U.S. Pat. No. 5,007,429 to Treatch et al. describes a user interface for direct programming of operating parameters for patient testing of blood pressure and downloading the data to an office control unit.

U.S. Pat. No. 5,019,974 to Beckers describes a diabetes management system and apparatus for efficient medical control for diabetes comprising a recorder, interface module, and master computer which can develop programs of therapy which can be downloaded to the recorder to remind the patient of pending therapy actions.

SUMMARY OF THE INVENTION

The invention overcomes the shortcomings of the prior art by providing a monitoring system designed specifically for communication with a communication module which facilitates data transfer with a remote site. The communication module has data input mechanisms to facilitate setting parameters of the monitoring system. The communication module more specifically has a modem member which is used to communicate with the remote site and an optional data exchange module which is designed to communicate the same information with a local computer system. The remote site is preferably a bulletin board system or internet site where the monitoring information can be stored by the patient using the monitoring system by patient identification or name and include monitoring readings, time and date stamp, conditions such as meal times, exercise times and therapy amounts and their associated date and time.

The communication module can comprise the data transfer mechanisms described above and may also contain data entry devices for inputting information such as time and date which can then be downloaded to the monitoring system to reset these parameters. Additional features which can be included in the communication module include function and data input keys to input other disease state information and a display for viewing this manually entered data.

The system may also be adapted to download from the remote site or a local computer time and date information to permit the communication module to automatically set or change the time and date system in the communication module and/or the monitoring device. One advantage of the invention is the simplification of the data capture method and the presence of a data collection system which is accessible by all patients to capture their data and permit it to be reviewed by their specific health care professional. An additional benefit is the simplification of the disease management by elimination of the need for noncomputer-trained patients to manually record all their data. Another benefit of the system is the reduction in size and the convenience provided by elimination of the data communication functions and elimination or reduction in size of the user interface means required to scroll through data stored in the monitor, set time and date, and communicate with current data management systems.

BRIEF DESCRIPTION OF THE DRAWINGS

Many objects and advantages of the present invention will be apparent to those skilled in the art with a reading of this specification in conjunction with the attached drawings, wherein like reference numerals are applied to like elements and wherein:

FIG. 1 is a schematic illustration of the communication module in accordance with an embodiment of the invention;

FIG. 2 is a schematic representation of a monitoring instrument in accordance with the invention;

FIG. 3 is a schematic representation of the communication module, the monitoring instrument and the remote locations in accordance with an embodiment of the invention;

FIG. 4 is a schematic representation of the communication module in communication with a local computer in accordance with the invention;

FIG. 5 is a schematic representation of a system in accordance with the invention in which a voice recognition system is employed;

FIG. 6 is a schematic representation of a communication module in connection with a monitoring instrument in accordance with the invention; and FIG. 7 is a schematic representation of the communication module in connection with the monitoring instrument and a remote location in accordance with the invention.

DESCRIPTION OF THE INVENTION

This invention provides physiological information collection and communication for patient disease management through the utilization of a system comprising a monitoring instrument, communication device and remote data collection site, thereby providing many benefits to patients controlling their disease state with intensive therapy. One such a task is the tight control of diabetes where the patient derives substantial benefit therefrom. Of course it is contemplated that the device can be used for testing for any analyte and it is not intended that the scope be limited to patient physiological data.

As seen in FIG. 3, an arrangement in accordance with the invention comprises a monitoring instrument 1 (FIG. 2) which can be used to gather physiological information during a collection mode. This physiological information may be the presence or concentration of an analyte of the patient, such as blood glucose level for diabetes control and treatment, or an analyte of urine or of intersticial fluid. The gathered information may be converted into information data and stored for uploading, via a communication module 11 during an interface mode, at a later time. The monitoring instrument 1 comprises a detection/analysis system 2 which is used to gather patient physiological data, such as blood glucose level, in any manner familiar to those skilled in the art, and may include optical testing of a sample on a sample strip impregnated with a suitable reagent. In such an optical arrangement, the analyte in the sample reacts with the reagent, with the reaction producing a physically detectable change which may entail an increase or decrease of a certain color component readily detectable via, for instance, electro-optical observation and measurement. LEDs and photodetectors may be used for this purpose in a well known manner. Alternatively, conductive probes may be used to measure the changed electrical conductivity between points on the sample strip due to the progression of the reaction of the analyte with the reagent.

As shown in FIG. 2, the monitoring instrument 1 is also equipped with a memory module 4 which is used for storing various information, including the gathered physiological information and instructions for proper operation of the monitoring instrument 1. Control of the monitoring instrument 1 is effected using a microprocessor 3 operating in conduction with a system clock 5. A rechargable battery pack or other power source (not shown) may be provided to furnish the necessary power for operation.

In practice the patient may use the monitoring instrument 1 for some number of times to effect the collection of the physiological information. Subsequently, the patient connects the monitoring instrument 1 with a communication module 11 (FIG. 1) which establishes communication with the monitoring instrument 1 and reads the data stored in the memory of the monitoring instrument 1 during an interface mode. The interface mode is illustrated schematically in FIG. 6. The connection between the monitoring instrument 1 and the communication module 11 can be via cable, using e.g., a connection port 12, or it may be more direct, through physical mating of the two devices such that associated leads or pins contact each other to establish an electrical connection. Other communication schemes between the two devices are also contemplated and may include optical or ultrasonic ("remote control") type connections. The interface mode may also entail a charging session concurrent with the other interface activities, such as the memory download, and would comprise the use of a battery charging system (not shown) provided in or with the communication module 11 which engages the battery pack of the monitoring instrument 1 for recharging thereof.

As shown in FIGS. 1 and 4, the communication module 11 comprises a microprocessor 13 which controls the operation of the various components, including a display 14, data entry means 15, transfer mode selection device 21, random access memory 18, read only memory 18, serial or parallel local computer system communication system 20 and modem system 16. The communicaton module 11 is provided with a telephone system connection means 17 and local system connection means 22 which effect the linking functions for connection and communication with remote locations such as sites 50 (FIG. 7) which may be an internet location or an electronic bulletin board, or a local computer 31 connected via, e.g., a cable link 32 (FIG. 4).

The patient can use display 14 of the communication module 11 to review the data, or the communication module can be permitted to automatically contact the remote site 50 or local computer 31 and transfer the data to a data storage system (not shown) provided at the remote location. Such automatic transfer would require little or no involvement by the patient—the communication module 11 senses the presence or connection of the monitoring instrument 1 thereto and automatically commences information transfer to the remote site 50 and/or local computer 31. The information exchange between the communication module 11 and the remote locations may be bidirectional, such that the data storage system at the remote location is capable of transferring correct time and date and other information to the communication module 11, which can use it to reset its clock and/or the clock in the monitoring device 1.

Two types of communication are selectable by the patient through the data entry means 15, which may be a control pad or key pad or other input mechanism. The patient, after connecting the monitoring instrument 1 with the communication module 11, can select either a local transfer (to, e.g., the local computer 31 as shown in FIG. 4) or a remote transfer of data to a data storage system disposed at the remote site 50 such as the internet site or electronic bulletin board (FIG. 7). As discussed above, it is contemplated that the transfer itself can be automatically activated upon completion of the connection process of the monitoring instrument 1 and the communication module 11, e.g., in a situation where these two components matingly engage each other, sensors can be provided which detect the successful fitting of the components to thereby commmence the transfer process. It is also contemplated that the processor in the monitoring instrument 1 can be used instead of a processor in the communication module 11 to control the communication module 11 and/or to control and transfer data. Similarly, the communication module 11 need not be equipped with both a modem module and a data transfer module—one or the other could suffice to serve both functions. The telephone system connection means 17 can be replaced with an alternate internet connection to facilitate communication with the remote site 50.

The system of the invention can also be configured with the appropriate user interface for user supplied information and/or review of the captured data. Such a user interface can be a keypad (not shown) with a display device. The system can also be configured to compensate for various handicaps such as vision or hearing impairments of the user. A vision-impaired system could have an attachment means to permit the use of a larger display or voice recognition and response system. Alternately, it may have the voice recognition system incorporated into the communication module, enabling the communication module to respond the user's voice commands. Such devices have been developed for various computer systems such as IBM compatible personal computers. FIG. 5 shows an embodiment in accordance with the invention in which a voice recognition system 40 supplements or replaces the communication module's display 14 and/or data entry system 15.

In operation, the patient uses the monitoring instrument 1 to determine his or her glucose level and the information, which is used to generate information data, is stored in the memory module 4 of the monitoring instrument along with the time and data information. Alternately, the patient may enter his or her exercise or insulin therapy and that action is time and date stamped and stored in the memory module 4, which may comprise a conventional RAM (random access memory) device. At a convenient time and possibly after a number of such events have been recorded by the monitoring instruments, the patient uses the communication port 12 and places the monitoring instrument 1 in communication with the communication module 11. Then, in a transmission mode, the patient selects the data storage system to where the data is to be transferred and initiates the data transfer, or the communication module 11 automatically initiates the transfer by sensing the monitoring instrument 1 as discussed above. The communication module 11 may be equipped to provide an indication that the transfer is in progress and initiates communication with the selected data storage system. The information data is read or transferred from the monitoring instrument 1 or stored in the communication module 11 random access memory 18 for transfer to the data storage system at a later time. If the data storage system is a remote site (50) such as bulletin board or internet site, the modem system 16 is initilized and communication protocol initiated between the communication module 11 and the compatible modem system (not shown) on the data storage system. If the system is to communicate with a local system, such as computer 31, the parallel or serial communication protocol is initiated with the local computer system 31. The information data is then transferred and the data storage system can transfer the correct time and date information back to the communication module 11 where it is used to update the communication module clock and/or the monitoring instrument clock 5. After the transfer is complete, the communication module 11 releases a transfer-in-progress indicator (not shown) and terminates the communication protocol with the data storage system. The monitoring system may be left in the communication module until needed by the patient while an optional charging circuit in the communication module recharges the batteries of the monitoring system prior to the next monitoring event.

The invention does not require the patient to have any knowledge of computerized systems to complete the download and transfer features, making the data collection available to a large number of patients who do not have or use a computer system. The data is automatically exchanged in this case via modem to the remote data collection site along with information identifying the patient and/or the medical professional who monitors the patient. This permits medical professionals the ability to review their patients' disease management state at intervals other than during regular appointments by e.g. logging into the data collection site via the bulletin board or internet connection. This provides many advantages to patients by permitting them to have a storage location which can be used to monitor the long-term control of their disease.

The remote or local data storage system collects the information which is transferred from the monitoring instrument 1 and synchronizes and compiles it to eliminate duplicates from frequent uploads and interleafing of monitoring results if the patient is using more than one monitoring instrument 1 as is contemplated. The time and data recording associated with each result may be used to accomplish this function. The data storage system associated with the invention can be developed from either relational or table driven database technologies, including software using Oracle™, Informix™, and Microsoft Access™ engines. The system can also work with a discrete file system using a data management sub-system to effectively handle the numerous files.

A typical layout of the associated data to be stored in the data storage module of the invention includes time, date, monitoring reading, calories eaten, insulin dosage, and time after exercise. However, many different pieces of information could be captured by a monitoring insturment 1 and transferred to the data storage system at the remote location 50 by operation of the system of the invention. The invention is intended to permit the patient to capture his or her disease state condition and store it for review and therapy modification.

One advantage of the invention is the simplification of the data capture method and the presence of a data collection system which is accessible by all patients to capture their data and permit it to be reviewed by their specific health care professional. An additional benefit is the simplification of the disease management by elimination of the need for noncomputer-trained patients to manually record all their data. Another benefit of the system is the reduction in size and the convenience provided by elimination of the data communication functions and elimination or reduction in size of the user interface required to scroll through data stored in the monitoring instrument 1, set time and date, and communicate with current data management systems. Another advantage is that the communication module 11 can be used to recharge the batteries in the monitoring 1 system to reduce the size of the device by minimizing the battery size.

In accordance with the invention, the monitoring instrument is designed or selected to work with the communication module 11. However, the communication module 11 can alternately be designed to work with a number of monitoring instruments for increased versatility. Similarly, it is possible to to eliminate the microprocessor 13 of communication module 11, along with random access memory 18 and use microprocessor 3 and memory module 4 of monitoring instrument 1. Additionally, the memory module 4 of the monitoring instrument can be designed to be removable such that it can interface, as a stand alone unit, with the communication module 11 to effect the information data exchange.

An advantage of the invention is the simplification of the data capture method and the presence of a data collection system which is accessible by all patients to capture their data and permits it to be reviewed by their specific health care professional. An additional benefit is the simplification of the disease management by elimination of the need for noncomputer-trained patients to manually record all their data. Another benefit of the system is the reduction in size and the convenience provided by elimination of the data communication functions and elimination or reduction in size of the user interface means required to scroll through data stored in the meter, set time and date, and communicate with current data management systems. Another advantage is that the communication module can be used to recharge the batteries in the monitoring system to reduce the size of the device by minimizing the battery size. The invention is intended to permit patients to capture their disease state condition and store them at local or remote locations for review and therapy modification.

The above are exemplary modes of carrying out the invention and are not intended to be limiting. It will be apparent to those skilled in the art that modifications thereto can be made without departure from the spirit and scope of the invention as set forth by the following claims.

What is claimed is:

1. A device for collecting and communicating analyte concentration information comprising:
   a monitoring instrument adapted to operate in a collection mode and an interface mode in accordance with predetermined parameters, the monitoring instrument receiving the analyte concentration information and generating and storing information data representative of the analyte concentration information in the collection mode; and
   a communication module adapted to operate in the interface mode and a transmission mode, the communication module interfacing with the monitoring instrument to download the information data from the monitoring instrument in the interface mode, the communication module selectively transmitting the information data to an internet site and/or an electronic bulletin board in the transmission mode, the communication module comprising:
      a communication port for effecting the interfacing of the communication module with the monitoring instrument;
      a communication means for effecting the transmission to the internet site and/or the an electronic bulletin board; and
      an input means capable of inputting at least a portion of the predetermined parameters to the communication module.

2. The device of claim 1, wherein the analyte concentration information is representative of the concentration of at least one blood analyte.

3. The device of claim 1, wherein the analyte concentration information is representative of blood glucose concentration.

4. The device of claim 1, wherein the analyte concentration information is representative of the concentration of at least one urine analyte.

5. The device of claim 1, wherein the analyte concentration information is representative of the concentration of at least one interstitial fluid analyte.

6. The device of claim 1, wherein the communication module comprises a display means for displaying the predetermined parameters and/or the information data.

7. The device of claim 6, wherein the input means is adapted to manipulate the displayed predetermined parameters and/or information data.

8. The device of claim 6, wherein one or both of the display means and the input means are adapted to compensate for vision impairment and/or hearing impairment.

9. The device of claim 1, further comprising a remote processing system adapted to manipulate the information data, the communication means comprising a data exchange module for effecting communication between the remote processing system and the communication module.

10. The device of claim 9, wherein the predetermined paramaters are input to the communication module from the remote processing system.

11. The device of claim 10, wherein the predetermined parameters comprise date and time entries.

12. The device of claim 11, wherein the remote processing system is adapted to synchronize and interleaf the information data according to the date and time entries and to sort the information data according to patient and/or medical professional identification information.

13. The device of claim 1, wherein the input means is a voice recognition system.

14. The device of claim 1, wherein the communication means comprises a modem.

15. The device claim 1, wherein the predetermined parameters are input to the communication module from the internet site and/or the electronic bulletin board.

16. The device of claim 15, wherein the predetermined parameters comprise time and date entries.

17. The device of claim 16, wherein the internet site and/or the electronic bulletin board are adapted to synchronize and interleaf the information data according to the date and time entries and to sort the information data according to patient and/or medical professional identification information.

18. The device of claim 16, wherein the information data includes one or more of monitoring readings, time and date stamps, meal times, exercise times, and therapy amounts.

19. The device of claim 1, wherein the monitoring instrument operates as a stand alone unit independent of the communication module in the collection mode and is adapted to effect multiple collection mode operations prior to operation in the interface mode.

20. The device of claim 1, wherein the monitoring instrument further comprises a battery rechargeable for powering the monitoring instrument, and wherein the communication module further comprises a battery recharger for charging the rechargeable in the interface mode.

21. The device of claim 1, wherein the internet site and/or the electronic bulletin board are adapted to be selected through the input means.

22. The device of claim 1, further comprising a processor for controlling the operation of the communication module.

23. The device of claim 22, wherein the processor is disposed in the monitoring instrument.

24. The device of claim 1, wherein the communication port is a first engaging portion disposed in the communication module and adapted to mate with a second engaging portion disposed on the monitoring instrument.

25. The device of claim 24, wherein the mating activates the interface mode.

26. The device of claim 24, wherein the mating activates the transmission mode.

27. The device of claim 1, wherein the communication port is a cable which plugs into the monitoring instrument and the communication module.

28. The device of claim 1, wherein the information data includes representations of one or more of monitoring readings, time and date stamps, meal times, exercise times, and therapy amounts.

29. A method for collecting and communicating analyte concentration information comprising:
gathering, in a collection mode, the analyte concentration information in a monitoring instrument;
generating, in the collection mode, information data representative of the analyte concentration information;
downloading, in an interfacing mode, the information data from the monitoring instrument to a communication module; and
selectively sending the information data, in a transmission mode, from the communication module to at least one of a internet site and an electronic bulletin board.

30. The method of claim 29, wherein the analyte concentration information is representative of the concentration of at least one blood analyte.

31. The method of claim 29, wherein the analyte concentration information is representative of blood glucose concentration.

32. The method of claim 29, wherein the analyte concentration information is representative of the concentration of at least one urine analyte.

33. The device of claim 29, wherein the analyte concentration information is representative of the concentration of at least one interstitial fluid analyte.

34. The method of claim 29, wherein the communication module is provided with a display means for displaying the information data.

35. The method of claim 29, further comprising the step of manipulating the information data using a remote processor disposed at a remote location.

36. The method of claim 29, wherein at least one of the collection, interfacing and transmission modes is governed by predetermined parameters communicated to the communication module from the internet site or electronic bulletin board.

37. The method of claim 36, wherein the predetermined parameters comprise date and time entries.

38. The method of claim 29, further comprising the step of storing the information data in an electronic bulletin board at said remote location.

39. The method of claim 29, further comprising the step of storing the information data at an internet site at said remote location.

40. The method of claim 29, wherein the information data includes one or more of monitoring readings, time and date stamps, meal times, exercise times, and therapy amounts.

41. The method of claim 29, wherein the monitoring instrument operates as a stand alone unit independent of the communication module in the collection mode and is adapted to effect multiple collection mode operations prior to operation in the interface mode.

42. The method of claim 29, wherein the monitoring instrument is provided with a rechargable battery for powering the monitoring instrument, and wherein the communication module is provided with a battery recharger for charging the rechargable battery in the interface mode.

43. The method of claim 29, wherein the step of selectively sending comprises using an input means to select the internet site or electronic bulletin board.

44. The method of claim 29, further comprising the step of using a processor for controlling the operation of the communication module.

45. The method of claim 29, wherein the processor is disposed in the monitoring instrument.

46. The method of claim 34, wherein the display means is adapted to compensate for vision impairment.

47. The method of claim 29, wherein the communication module is responsive to voice commands.

48. The method of claim 34, wherein the display means is adapted to compensate for hearing impairment.

49. The method of claim 35, wherein at least one of the collection, interfacing and transmission modes is governed by predetermined parameters communicated to the communication means, the pretermined parameters comprising date and time entries, and wherein the remote processing system is adapted to synchronize and interleaf the information data according to the date and time entries.

50. The method of claim 38, wherein at least one of the collection, interfacing and transmission modes is governed by predetermined parameters communicated to the communication means, the predetermined parameters comprising date and time entries, and wherein the information data is synchronized and interleafed at the electronic bulletin board according to the date and time entries.

51. The method of claim 39, wherein at least one of the collection, interfacing and transmission modes is governed by predetermined parameters communicated to the communication means, the predetermined parameters comprising date and time entries, and wherein the information data is synchronized and interleafed at the internet site according to the date and time entries.

52. The method of claim 29, wherein the interfacing mode is effected using a communication port.

53. The method of claim 52, wherein the communication port is a cable adapted to plug into the monitoring instrument and the communication module.

54. The method of claim 52, wherein the communication port is a first engaging portion disposed in the communication module and adapted to mate with a second engaging portion disposed on the monitoring instrument.

55. The method of claim 54, wherein the mating activates the interface mode.

56. The method of claim 54, wherein the mating activates the transmission mode.

57. A device for collecting and communicating analyte concentration information comprising:
a monitoring instrument adapted to operate in a collection mode and an interface mode in accordance with predetermined parameters, the monitoring instrument receiving the analyte concentration information and generating and storing information data representative of the analyte concentration information in the collection mode, the information being stored in a removable memory module of the monitoring instrument; and
a communication module adapted to operate in the interface mode and a transmission mode, the communication module interfacing with the memory moudlue of the monitoring instrument to download the information data from the memory module in the interface mode, the communication module selectively transmitting the information data to one or more locations remote from the communication module in the transmission mode, the communication module comprising:
a communication port for effecting the interfacing of the communication module with the memory module of the monitoring instrument;
a communication means for effecting the transmission to the one or more remote locations; and
an input means capable of inputting at least a portion of the predetermined parameters to the communication module.

58. A device for collecting and communicating analyte concentration information comprising:

a monitoring instrument having a first engaging portion and adapted to operate in a collection mode and an interface mode in accordance with predetermined parameters, the monitoring instrument receiving the analyte concentration information and generating and storing information data representative of the analyte concentration information in the collection mode; and a communication module adapted to operate in the interface mode and a transmission mode, the communication module interfacing with the monitoring instrument to download the information data from the monitoring instrument in the interface mode, the communication module selectively transmitting the information data to one or more locations remote from the communication module in the transmission mode, the communication module comprising:

a communication port for effecting the interfacing of the communication module with the monitoring instrument, the communication port comprising a second engaging portion adapted to mate with the first engaging portion to thereby activate at least one of the interface and transmission modes;

a communication means for effecting the transmission to the one or more remote locations; and an input means capable of inputting at least a portion of the predetermined parameters to the communication module.

59. A device for collecting and communicating analyte concentration information comprising:

a monitoring instrument adapted to operate in a collection mode and an interface mode in accordance with predetermined parameters, the monitoring instrument receiving the analyte concentration information and generating and storing information data representative of the analyte concentration information in the collection mode, the monitoring instrument having a processor for controlling operation of the monitoring instrument; and a communication module detachable from the monitoring instrument and adapted to operate in the interface mode and a transmission mode, the communication module being controlled by said processor and interfacing with the monitoring instrument to download the information data from the monitoring instrument in the interface mode, the communication module selectively transmitting the information data to one or more locations remote from the communication module in the transmission mode, the communication module comprising:

a communication port for effecting the interfacing of the communication module with the monitoring instrument;

a communication means for effecting the transmission to the one or more remote locations; and an input means capable of inputting at least a portion of the predetermined parameters to the communication module.

* * * * *